United States Patent [19]

Mori et al.

[11] Patent Number: 5,013,715

[45] Date of Patent: May 7, 1991

[54] PASTY ORGANOPOLYSILOXANE COMPOSITION

[75] Inventors: Shigeru Mori; Satoshi Kuwata, both of Gunma, Japan

[73] Assignee: Shin-Etsu Chemical Co., Ltd., Tokyo, Japan

[21] Appl. No.: 172,689

[22] Filed: Mar. 24, 1988

[30] Foreign Application Priority Data

Mar. 24, 1987 [JP] Japan ................................ 62-69592

[51] Int. Cl.$^5$ ................................................ A61K 31/00
[52] U.S. Cl. ........................................ 514/53; 514/23; 514/63
[58] Field of Search ............... 514/23, 63, 72, 880, 514/844, 846; 424/71, 70, 78; 252/573

[56] References Cited

U.S. PATENT DOCUMENTS

| | | | |
|---|---|---|---|
| 4,411,933 | 10/1983 | Samejima et al. | 424/495 |
| 4,423,032 | 12/1983 | Abe et al. | 514/63 |
| 4,770,873 | 9/1988 | Wolfram et al. | 424/71 |
| 4,780,145 | 10/1988 | Mori et al. | 106/206 |
| 4,894,224 | 1/1990 | Kuwata et al. | 514/772 |

*Primary Examiner*—Ronald W. Griffin
*Assistant Examiner*—Everett White
*Attorney, Agent, or Firm*—Millen, White & Zelano

[57] ABSTRACT

The pasty organopolysiloxane composition is compounded from a methyl phenyl polysiloxane fluid and 5 to 50% by weight of a fatty acid ester of saccharose. The composition is highly transparent and useful as a base of various kinds of pasty preparations for cosmetic and medicinal uses to give an advantage of refreshed feeling without stickiness to the person using the preparation by applying to the skin after wiping off because the composition is free from the problem of powdery residue when the preparation on the skin has been wiped off.

8 Claims, No Drawings

PASTY ORGANOPOLYSILOXANE COMPOSITION

BACKGROUND OF THE INVENTION

The present invention relate to a pasty organopolysiloxane composition or, more particularly, to an organopolysiloxane composition having a pasty consistency and which is useful as a base material of various kinds of pasty preparations for cosmetic and medicinal uses without formulating any fine powdery material.

As is known, pasty composition formulated with a silicone oil, i.e. organopolysiloxane fluid, are widely used as a base material of various kinds of pasty preparations for cosmetic and medicinal uses such as creams, hair-dressings, ointments and the like. In the formulation of such an organopolysiloxane composition, it is usual that a silicone oil is imparted with the pasty consistency by compounding with a finely divided powder such as finely divided silica filler, optionally, after a hydrophobic surface treatment, surface-treated bentonite and the like in a considerably large amount.

These silicone-based pasty compositions have several problems and disadvantages in respect of the practical applicability. One of the problems is their low transparency as a consequence of the formulation of a powdery ingredient which decreases the commercial value of the product, which should desirably have aesthetically acceptable high transparency. The transparency of the compositions can be improved to some extent by suitably selecting the types of the silicone oil and the powdery material but no highly transparent composition can be obtained in the prior art. Another more serious problem in these prior art compositions is that, when a preparation compounded with the composition is applied to human skin and then wiped off, the powdery ingredient contained therein is left on the skin which more or less gives an unpleasant feeling and a poor appearance. Accordingly, a pasty organopolysiloxane composition suitable as a base material of cosmetic and medicinal preparations is desired without compounding a powdery material therein.

SUMMARY OF THE INVENTION

The pasty organopolysiloxane composition of the present invention, which has been completed as a result of the extensive investigations undertaken with an object to solve the above described problems in the prior art, comprises, in admixture;

(A) a methyl phenyl polysiloxane fluid represented by the average unit formula $$R_aSiO_{(4-a)/2}, \qquad (I)$$

in which R is a methyl group or phenyl group, at least one of the groups denoted by R in a molecule being phenyl, and the subscript a is a positive number in the range from 2 to 3, and having a viscosity in the range from 4 to 1000 centistokes at 25° C.; and (B) a fatty acid ester of saccharose in an amount in the range from 5 to 50 parts by weight per 100 parts by weight of the component (A).

Optionally, the methyl phenyl polysiloxane as the component (A) in the above defined formulation of the inventive composition can be partially replaced with a cyclic poly(dimethyl siloxane) having a degree of polymerization of 3 to 6 and/or a linear poly(dimethyl siloxane) having a degree of polymerization not exceeding 650 excepting the terminal groups, which may be a silanolic hydroxy group or a trimethyl silyl group, in an amount of 80% by weight or smaller as a total of the cyclic and linear poly(dimethyl siloxanes) based on the overall amount of the component (A).

DETAILED DESCRIPTION OF THE PREFERRED EMBODIMENTS

As is described above, the essential ingredients in the inventive composition are the methyl phenyl polysiloxane fluid as the component (A) and the fatty acid ester of saccharose as the component (B). The composition compounded with these components in the above specified weight proportion has a pasty consistency suitable as a base of various kinds of pasty preparations for cosmetic and medicinal uses. The preparation compounded with the inventive composition is capable of giving a more pleasant feeling of use to the person using the same by applying it to his or her skin in respect of stickiness and refreshingness after use than the conventional preparations obtained by compounding petrolatums, liquid paraffins, vegetable oils and the like. The composition of the invention has high transparency not to decrease the beautiful appearance of the preparations compounded therewith. Needless to say, the preparations compounded with the inventive composition are absolutely free from the problem causes by the powdery residue on the skin when the preparation is applied to the skin and then wiped off because no powdery ingredient is contained in the composition.

The component (A) as the base ingredient of the inventive composition is a methyl phenyl polysiloxane fluid represented by the average unit formula $$R_aSiO_{(4-a)/2}, \qquad (I)$$

in which R is a methyl group or phenyl group, at least one of the groups denoted by R in a molecule being phenyl, and the subscript a is a positive number in the range from 2 to 3. It is preferable that from 5 to 50% or, more preferably, from 10 to 40% by moles of the groups denoted by R, i.e. methyl and phenyl groups, are phenyl groups. When all of the groups denoted by R are methyl groups, no pasty consistency can be obtained by compounding the polysiloxane fluid with a fatty acid ester of saccharose as the component (B). The methyl phenyl polysiloxane fluid should have a viscosity in the range from 4 to 1000 centistokes or, preferably, not to exceed 100 centistokes or, more preferably, not to exceed 50 centistokes at 25° C. When the viscosity of the methyl phenyl polysiloxane fluid is too low, the composition prepared from the methyl phenyl polysiloxane and the fatty acid ester of saccharose has no sufficiently high consistency and good spreadability as a pasty material unless the proportion of the fatty acid ester of saccharose is unduly increased. When the viscosity of the methyl phenyl polysiloxane fluid is too high, on the other hand, the composition may have some stickiness so that the cosmetic or medicinal preparation compounded therewith cannot give a refreshed feeling to the person using the same.

As is mentioned above, the methyl phenyl polysiloxane fluid as the base ingredient of the inventive composition may be partly replaced with a cyclic poly(dimethyl siloxane) and/or a linear poly(dimethyl siloxane) to form the component (A) in combination although at least 20% by weight of the component (A)

should be the above defined methyl phenyl polysiloxane fluid. When the proportion of the methyl phenyl polysiloxane fluid in the component (A) is lower than 20% by weight, the combined polysiloxanes may have poor miscibility with the fatty acid ester of saccharose so that no uniform pasty composition can be obtained at least at room temperature. It is also desirable that the proportion of either one of the cyclic and linear poly(dimethyl siloxanes) does not exceed 50% by weight based on the overall amount of the component (A) as a combination of the methyl phenyl polysiloxane and cyclic and linear poly(dimethyl siloxanes).

The above mentioned cyclic poly(dimethyl siloxane) is a compound represented by the general formula

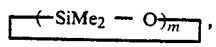 , (II)

in which Me is a methyl group and the subscript m is a positive integer of 3 to 6. The cyclic poly(dimethyl siloxane) includes hexamethyl cyclotrisiloxane, octamethyl cyclotetrasiloxane, decamethyl cyclopentasiloxane and dodecamethyl cyclohexasiloxane. The linear poly(dimethyl siloxane) is represented by the general formula

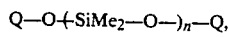 (III)

in which Me is a methyl group, Q is a hydrogen atom or a trimethyl silyl group and the subscript n is a positive integer in the range from 2 to 650.

The component (B) compounded with the above described component (A) is a fatty acid ester of saccharose and acts as a thickening agent to give a uniform pasty mixture. The fatty acid with which saccharose is esterified to give the ester as the component (B) is preferably a long-chain carboxylic acid free from unsaturation such as lauric acid, myristic acid, palmitic acid, stearic acid and the like although the saccharose ester may be a mixed ester with one or more of these long-chain carboxylic acids and a minor amount of a lower carboxylic acid such as acetic and propionic acids. The fatty acid ester of saccharose as the component (B) should preferably have a hydroxyl value not exceeding 200 because a fatty acid ester of saccharose having a hydroxyl value exceeding 200 is less compatible with the organopolysiloxane fluid as the component (A). The amount of the fatty acid ester of saccharose as the component (B) in the inventive composition is in the range from 5 to 50 parts by weight or, preferably, from 10 to 30 parts by weight per 100 parts by weight of the component (A), i.e. the methyl phenyl polysiloxane fluid, optionally in combination with the cyclic and/or linear poly(dimethyl siloxanes). When the amount of the saccharose ester is too small, the composition may have no sufficiently high consistency as a pasty material. When the amount thereof is too large, on the other hand, the consistency of the composition is too high to unduly decrease the spreadability of the preparations compounded with the composition on the skin.

The inventive organopolysiloxane composition can be prepared by mixing the components (A) and (B) each in a calculated and weighed amount to satisfy the specified proportion until a uniform mixture is obtained. It is advantageous that the mixing work of the components is performed at an elevated temperature in the range from 50° to 100° C. in order to accelerate uniformization of the mixture. For example, the components (A) and (B) are mixed together at about 100° C. to give a uniform mixture by dissolving the fatty acid ester of saccharose in the polysiloxane fluid and then the mixture is allowed to cool to room temperature so that the desired clear and pasty composition can be obtained easily and rapidly. The thus obtained composition of the invention is admixed with cosmetically or medicinally effective ingredients together with other optional additives such as oiliness improvers, perfumes, antioxidants, coloring agents and the like to give a cosmetic or medicinal preparation.

In the following, the pasty organopolysiloxane composition of the invention is described in more detail by way of examples, in which the term of "parts" always refers to "parts by weight" and the values of viscosity are all those obtained by the measurement at 25° C.

EXAMPLE 1

A mixture was prepared from 100 parts of a methyl phenyl polysiloxane fluid having a viscosity of 20 centistokes, of which the content of phenyl groups was 25 % by moles based on the overall amount of the methyl and phenyl groups, and 13 parts of a fatty acid ester of saccharose having a hydroxyl value of 20 (Sugar Wax A-10E, a product of Dai-ichi Kogyo Seiyaku Co.) which was a mixed ester of saccharose with stearic, palmitic and acetic acids in a molar ratio of 3.2:1.3:3.5. The mixture was melted together by heating at 60° to 70° C. and agitating for 15 minutes with a stirrer driven at a velocity of 200 rpm. The mixture is then allowed to cool to room temperature with the heater removed and rotation of the stirrer interrupted. A highly transparent, light-yellow pasty composition was obtained which had a consistency of 310 as determined according to the procedure specified in JIS K 2220.

EXAMPLE 2

The formulation and procedure for the preparation of the composition were substantially the same as in Example 1 except that the amount of the saccharose ester was decreased to 10 parts. The appearance of the composition thus obtained was similar to that prepared in Example 1 and the consistency thereof was 410.

EXAMPLE 3

The formulation and procedure for the preparation of the composition were substantially the same as in Example 1 except that the amount of the methyl phenyl polysiloxane fluid was decreased to 70 parts and, instead, 30 parts of decamethyl cyclopentasiloxane were additionally added and the amount of the saccharose ester was increased to 15 parts. The appearance of the composition thus obtained was similar to that prepared in Example 1 and the consistency thereof was 290.

EXAMPLE 4

The formulation and procedure for the preparation of the composition were substantially the same as in Example 1 except that 100 parts of the methyl phenyl polysiloxane fluid were replaced with a combination of 80 parts of 1,1,1,5,5,5-hexamethyl-3,3-diphenyl trisiloxane and 20 parts of octamethyl cyclotetrasiloxane and the amount of the saccharose ester was increased to 20 parts. The appearance of the composition thus obtained was similar to that prepared in Example 1 and the consistency thereof was 240.

EXAMPLE 5

The formulation and procedure for the preparation of the composition were substantially the same as in Example 1 except that 100 parts of the methyl phenyl polysiloxane fluid were replaced with a combination of 70 parts of 1,1,1,5,5,5-hexamethyl-3,3-diphenyl trisiloxane and 30 parts of dodecamethyl pentasiloxane and the amount of the saccharose ester was slightly decreased to 12 parts. The appearance of the composition thus obtained was similar to that prepared in Example 1 and the consistency thereof was 350.

COMPARATIVE EXAMPLE 1

The formulation and procedure for the preparation of the composition were substantially the same as in Example 1 except that the amount of the saccharose ester was decreased to 4 parts. Although a slight increase was noted in the viscosity of the polysiloxane fluid, no pasty composition could be obtained.

COMPARATIVE EXAMPLE 2

The formulation and procedure for the preparation of the composition were substantially the same as in Example 1 except that 100 parts of the methyl phenyl polysiloxane fluid were replaced with a combination of 15 parts of the same methyl phenyl polysiloxane fluid and 85 parts of decamethyl cyclopentasiloxane and the amount of the saccharose ester was increased to 20 parts. The saccharose ester could be dissolved in the polysiloxane fluid only incompletely so that phase separation took place in the composition after cooling to room temperature into precipitates of the saccharose ester and the polysiloxane fluid of which almost no increase was noted in the viscosity as compared to the fresh polysiloxane fluid.

What is claimed is:

1. A pasty organopolysiloxane composition adapted for use as a base for pasty cosmetic and pharmaceutical preparations, substantially free from solids which leave a powdery residue on a surface to which the composition is applied and which consists essentially of, in admixture:

(A) a polysiloxane component which is (i) a methyl phenyl polysiloxane fluid represented by the average unit formula $$R_a SiO_{(4-a)/2}$$

in which R is a methyl group or phenyl group, at least one of the groups denoted by R in a molecule being phenyl, and the subscript a is a positive number in the range from 2 to 3, and having a viscosity in the range from 4 to 1000 centistokes at 25° C.; or (ii) a mixture of (i) and up to 80% by weight of (i) of a cyclic poly(dimethyl siloxane) having a degree of polymerization of 3 to 6, a linear poly(dimethyl siloxane) having a degree of polymerization not exceeding 650 excepting the terminal groups, the terminal group being a silanolic hydroxy group or a trimethyl silyl group; and (B) a fatty acid ester of saccharose in an amount in the range from 5 to 50 parts by weight per 100 parts by weight of the component.

2. The pasty organopolysiloxane composition as claimed in claim 1 wherein the methyl phenyl polysiloxane fluid as the component (A) has a viscosity in the range from 4 to 50 centistokes at 25° C.

3. The pasty organopolysiloxane composition as claimed in claim 1 wherein from 5 to 50% by moles of the groups denoted by R in the component (A) are phenyl groups.

4. The pasty organopolysiloxane composition as claimed in claim 1 wherein the polysiloxane component (A) is a mixture as defined in (ii).

5. The pasty organopolysiloxane composition as claimed in claim 2 wherein the fatty acid ester of saccharose has a hydroxyl value not exceeding 200.

6. The pasty organopolysiloxane composition as claimed in claim 2 wherein the amount of the fatty acid ester of saccharose as the component (B) is in the range from 10 to 30 parts by weight per 100 parts by weight of the component (A).

7. The pasty organopolysiloxane composition as claimed in claim 2, wherein the fatty acid ester of saccharose has a hydroxyl value not exceeding 200; wherein the amount of the fatty acid ester of saccharose as the component (B) is in the range from 10 to 30 parts by weight per 100 parts by weight of the component (A); wherein the methyl phenyl polysiloxane fluid as the component (A) has a viscosity in the range from 4 to 50 centistokes at 25° C.; and wherein from 5 to 505 by moles of the groups denoted by R in the component (A) are phenyl groups.

8. A process for producing the pasty position as claimed in claim 1, which comprises the steps of mixing components (A) and (B) above the melting point of the mixture and then cooling the resulting mixture.

* * * * *